United States Patent
Spahn et al.

(10) Patent No.: US 7,202,481 B2
(45) Date of Patent: Apr. 10, 2007

(54) X-RAY DETECTOR

(75) Inventors: Martin Spahn, Erlangen (DE);
Thomas Schmitt, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 174 days.

(21) Appl. No.: 10/937,260

(22) Filed: Sep. 10, 2004

(65) Prior Publication Data
US 2005/0056789 A1    Mar. 17, 2005

(30) Foreign Application Priority Data
Sep. 12, 2003   (DE) .............. 103 42 197
May 10, 2004    (DE) .............. 10 2004 022 901

(51) Int. Cl.
*G01T 1/24*   (2006.01)
(52) U.S. Cl. ................... 250/370.09; 250/580
(58) Field of Classification Search ........ 250/370.09, 250/370.11, 370.01, 580, 336.1; 378/98.8, 378/189
See application file for complete search history.

(56) References Cited

U.S. PATENT DOCUMENTS

| | | | | |
|---|---|---|---|---|
| 5,381,014 A | * | 1/1995 | Jeromin et al. | 250/370.09 |
| 5,804,832 A | * | 9/1998 | Crowell et al. | 250/580 |
| 6,627,896 B1 | * | 9/2003 | Hashimoto et al. | 250/370.11 |
| 6,825,472 B2 | * | 11/2004 | Endo | 250/370.09 |
| 6,897,449 B1 | * | 5/2005 | Hata | 250/370.11 |
| 6,967,333 B2 | * | 11/2005 | Hata | 250/370.11 |
| 6,972,410 B2 | * | 12/2005 | Takeda | 250/370.09 |
| 7,057,181 B2 | * | 6/2006 | Yagi | 250/370.09 |
| 2002/0005490 A1 | * | 1/2002 | Watanabe | 250/370.09 |
| 2002/0030400 A1 | | 3/2002 | Frederick et al. | |
| 2004/0227096 A1 | * | 11/2004 | Yagi | 250/370.09 |

FOREIGN PATENT DOCUMENTS

DE    199 21 992 A1    11/2000
WO    WO 03/083512 A2    10/2003

OTHER PUBLICATIONS

M. Spahn et al., "Flachbilddetektoren in der Röntgendiagnostik", Radiologe 2003. 43:340-350.

* cited by examiner

*Primary Examiner*—David Porta
*Assistant Examiner*—Faye Boosalis
(74) *Attorney, Agent, or Firm*—Harness, Dickey & Pierce, P.L.C.

(57) ABSTRACT

An x-ray detector includes a detector plate having a multiplicity of detector elements arranged in the X direction and the Y direction, accommodated in a housing. To increase the robustness, the detector plate is accommodated in the housing in a floating manner by using at least one damping element.

12 Claims, 5 Drawing Sheets

X-RAY DETECTOR

The present application hereby claims priority under 35 U.S.C. §119 on German patent application numbers DE 103 42 197.1 filed Sep. 12, 2003, and DE 10 2004 022 901.5 filed May 10, 2004, the entire contents of each of which are hereby incorporated herein by reference.

FIELD OF THE INVENTION

The invention generally relates to an x-ray detector.

BACKGROUND OF THE INVENTION

X-ray detectors are known from Spahn, M. et al., Radiologe 2003, 43:340–350, for example. These are so-called solid-state or flat detectors. Of these, a distinction is made between flat detectors with an indirectly converting converter layer and flat detectors with a directly converting converter layer.

Flat detectors with an indirectly converting converter layer have a detector matrix which is formed by a multiplicity of photodiodes and is produced for example from amorphous silicon. The detector matrix is superposed by a converter layer formed by a scintillator. Incident x-ray radiation is converted into light in the scintillator. The light is sensed by the detector matrix located underneath.

Flat detectors with a directly converting converter layer have a detector matrix formed by a multiplicity of charge detectors, which is likewise produced from amorphous silicon. The detector matrix is superposed by a layer formed for example from amorphous selenium. Incident x-rays are converted into charges in the layer formed from amorphous selenium. The charges are sensed by the detector matrix located underneath.

Other flat detectors, for example Charge Coupled Devices (CCDs), Active Pixel Sensors (APSs) or CMOS chips, are also suitable for x-ray imaging.

The flat detectors known from the prior art are not particularly robust. Under mechanical loading, for example instances of impact, vibration and the like, they may be destroyed.

SUMMARY OF THE INVENTION

An object of an embodiment of the invention is to reduce or even eliminate at least one of the disadvantages of the prior art. One intention of at least one embodiment, in particular, is to provide an x-ray detector which is as simple to produce as possible and is as robust as possible.

An embodiment of the invention provides that the detector plate is accommodated in the housing in a floating manner by use of at least one damping element. This allows a robust x-ray detector to be provided in a surprisingly simple and low-cost way.

The housing may be a cassette. In this case, it is possible to produce mobile x-ray detectors in a simple way by using known flat detectors.

The detector plate expediently has a substrate, preferably produced from glass. Detector elements produced from amorphous silicon can be applied to the substrate.

According to a further configurational feature of at least one embodiment, electronics connected downstream of the detector elements may be accommodated in the housing. The electronics serve, inter alia, for reading out the charges picked up by the detector elements, for digitizing the signals, for amplification, for evaluation, for correction, etc. The electronics may be expediently accommodated on at least one further substrate or a printed circuit board. The further substrate may be applied to the detector plate and/or to the housing.

The detector plate may be advantageously attached by way of the damping element to the inside wall of the housing and/or to the further substrate. The damping element may peripherally surround the edge of the detector plate and/or the substrate. The damping element may in this case be formed as a peripheral shock absorber in the manner of a bumper known from automobile construction.

The damping element may be produced from a material, in particular a flexible material, which can absorb impact energy by deforming. It is particularly advantageous if the material has at least one hollow chamber. The hollow chamber contributes to the damping of vibrations or impact. It may be filled with air or a gel. The damping element advantageously has a medium selected from the following group: a soft foam sheet, a spring element or rubber element, a rubber-metal element, a liquid-damped element or gas-damped element.

BRIEF DESCRIPTION OF THE DRAWINGS

The present invention will become more fully understood from the detailed description of the exemplary embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
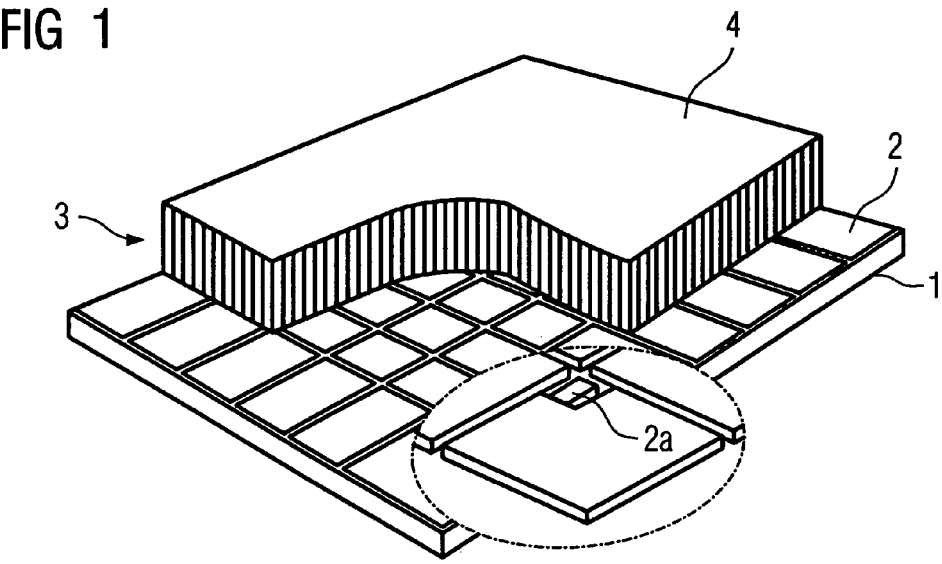
FIG. 1 shows a perspective, partly broken view of an x-ray detector according to the prior art.

In the case of the x-ray or flat detector shown in FIG. 1, a multiplicity of detector elements 2 are accommodated on a substrate 1, which is produced for example from glass. The detector elements 2 may be photodiodes produced from amorphous silicon. The detector elements 2 form a matrix in an X direction and a Y direction. Each of the detector elements 2 has a switch 2a. Applied to the detector elements 2 is a converter layer 4, which is produced for example from a luminescent material. This may be, for example, CsJ. The arrangement formed by the substrate 1, the detector elements 2 and the converter layer 4 is referred to hereafter as the detector plate 3.

Figure 2:
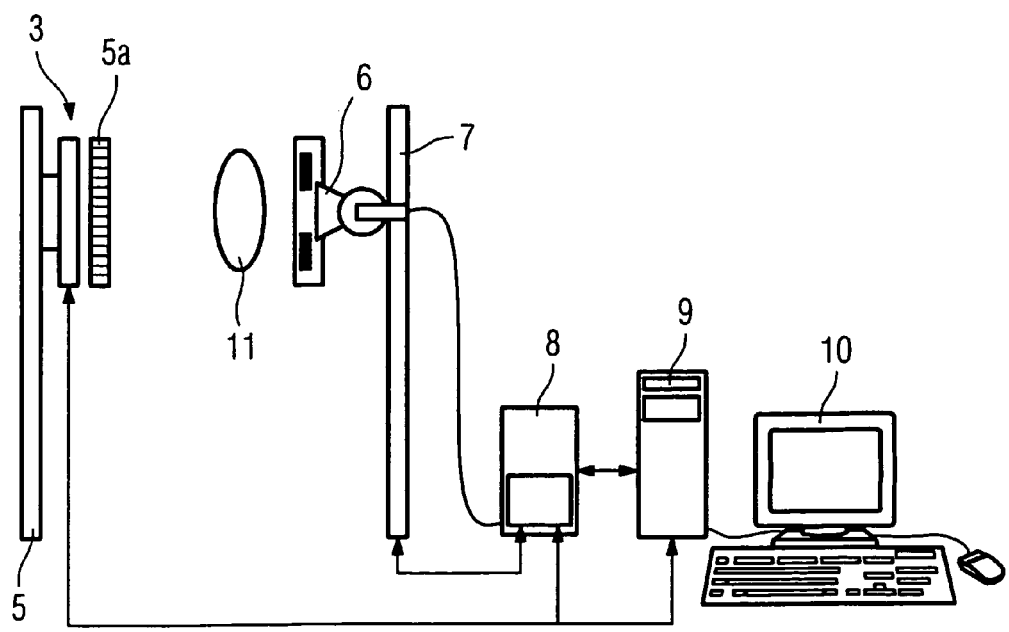
FIG. 2 shows a schematic view of an x-ray device according to the prior art.

FIG. 2 shows a schematic view of an x-ray device according to the prior art, using the x-ray detector shown in FIG. 1. The x-ray detector is fastened to a stand 5. It is accommodated in a housing. Arranged upstream of the x-ray detector on the radiation entry side is an anti-scatter grid 5a. An x-ray source 6 is accommodated on a further stand 7. The x-ray source 6 is connected to a high-voltage source 8. The high-voltage source 8 and the detector plate 3 are respectively connected to a computer 9 for controlling the x-ray device and for image evaluation. The reference numeral 10 designates a monitor and the reference numeral 11 designates an object located in the path of rays.

Figure 3:
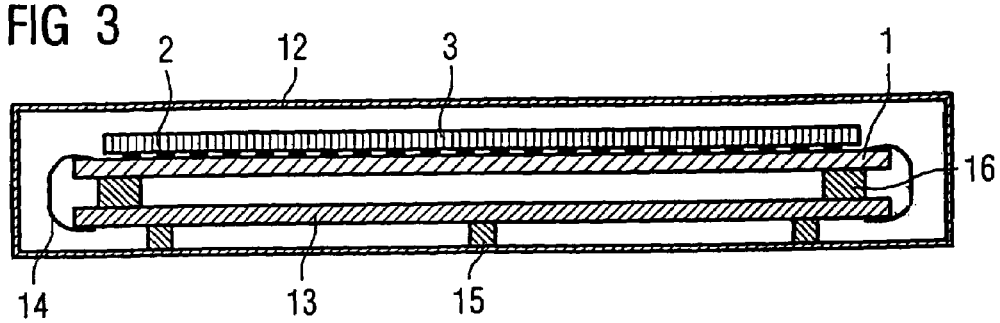
FIG. 3 shows a schematic sectional view of a further x-ray detector according to the prior art.

FIG. 3 shows a further x-ray detector according to the prior art. In this case, the detector plate 3 is accommodated in a housing 12. The housing 12 may be a cassette which is produced for example from metal, plastic, carbon fibers or a combination of these. Also accommodated in the housing 12 is a further substrate 13 with electronics (not shown here). The electronics are connected to the detector elements 2 by means of flexible leads 14. Instead of the leads 14, the detector elements 2 may of course also be connected to the electronics by means of via holes, bonding contacts, plug-in contacts or the like. The further substrate 13 is firmly attached to the inside wall of the housing 12 by means of rigid fastening means 15. The substrate 1 is rigidly mounted on the further substrate 13 by means of further rigid fastening means 16.

Figure 4:
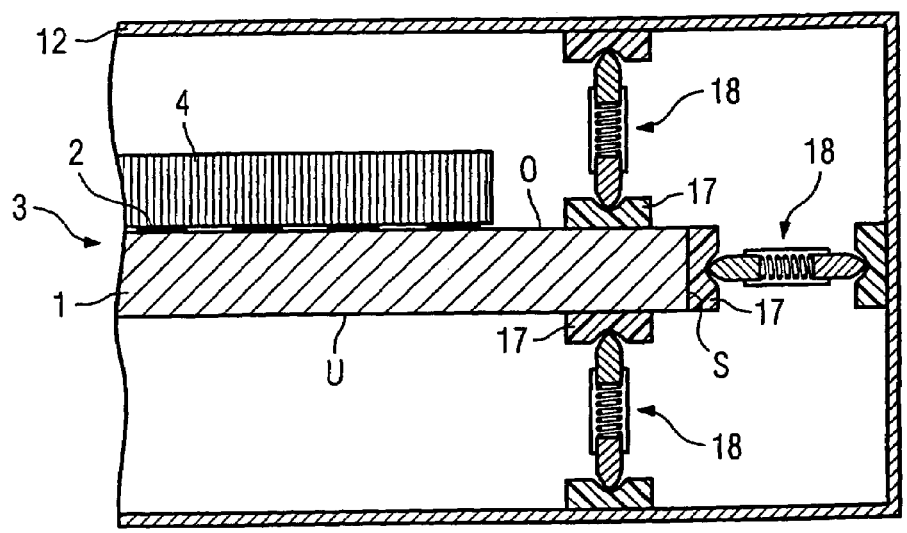
FIG. 4 shows a schematic partial sectional view of a first x-ray detector.

In FIG. 4, receiving elements 17 are attached to an upper side O, an underside U and a side edge S of the substrate 1. These may be plastic or rubber elements, which are connected to the substrate 1 by means of an adhesive bond. Receiving elements 17 of this type are likewise attached to the opposite inner side of the housing 12. Respectively accommodated between two opposing receiving elements 17 is a spring element 18.

The detector plate 3 is in this way mounted in the housing 12 in a floating manner (not shown here) in the regions of its four corners. In this case, the spring elements 18 are fitted under compressive stress. This facilitates mounting. No further fastening elements are required for fastening the spring elements 18. The securement of the spring elements 18 in the receiving elements 17 permits movement of the detector plate 3 in all directions.

Figure 5:
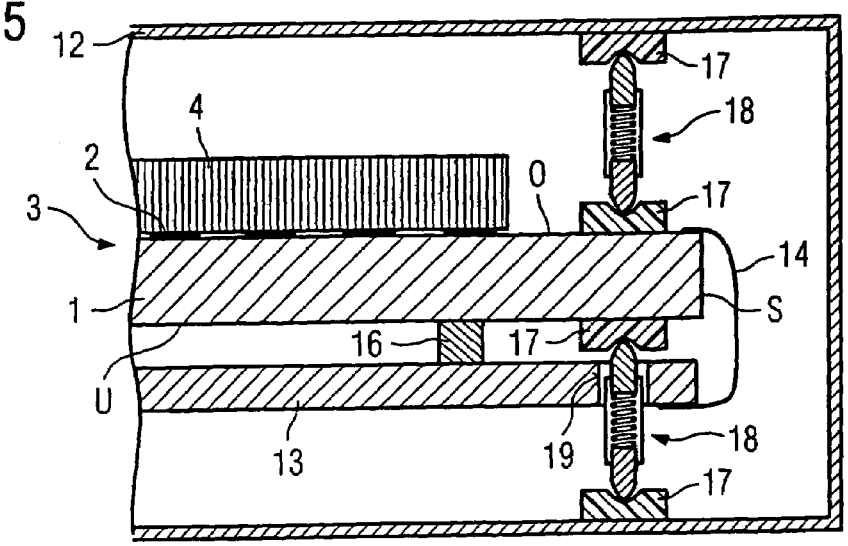
FIG. 5 shows a schematic partial sectional view of a second x-ray detector.

In the case of the second x-ray detector, shown in FIG. 5, the further substrate 13, having the evaluation electronics, is connected to the underside U of the substrate 1 by way of the further rigid fastening element(s) 16. Here, a lower spring element 18 is led through an aperture 19 in the further substrate 13. Apertures of this type may be provided at all the corners of the further substrate 13. Instead of the apertures 19, suitable clearances may of course also be provided. With the embodiment proposed, both the detector plate 3 and the evaluation electronics are mounted in the housing 12 in a floating manner.

Figure 6:
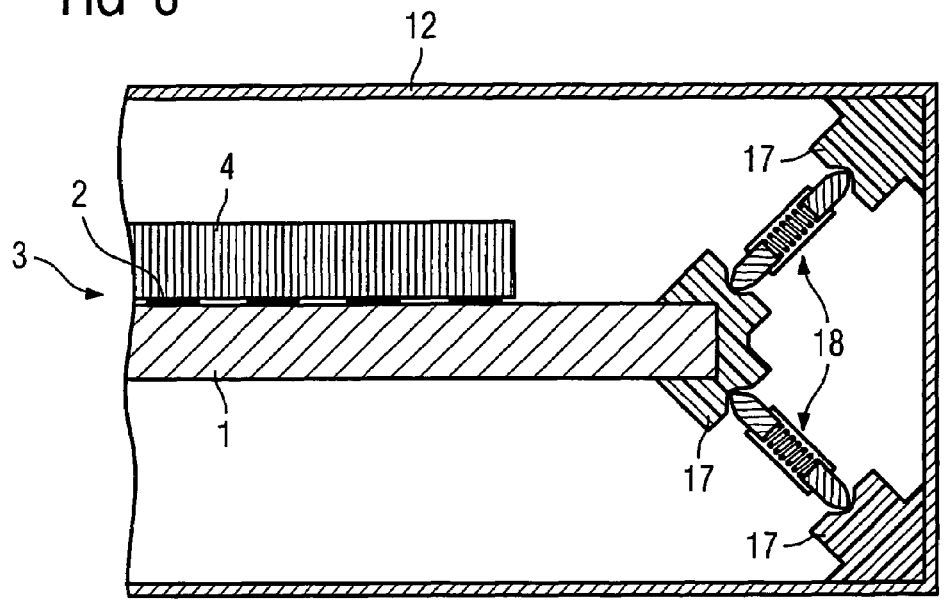
FIG. 6 shows a schematic partial sectional view of a third x-ray detector.

In the case of the third x-ray detector, shown in FIG. 6, the receiving elements 17 are attached in the corners of the housing 12. On the detector plate side, the receiving elements 17 may in this case be made in one piece, which is produced for example from injection-molded plastic. In this case, the receiving elements 17 may for example be simply clipped onto the corner of the substrate 1.

Figure 7:
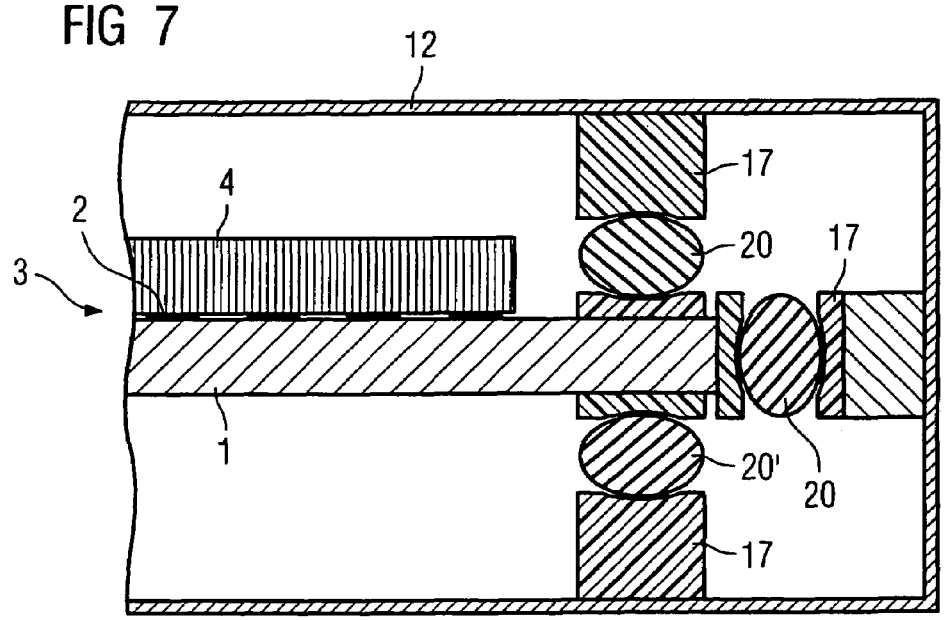
FIG. 7 shows a schematic partial sectional view of a fourth x-ray detector.
Figure 8:
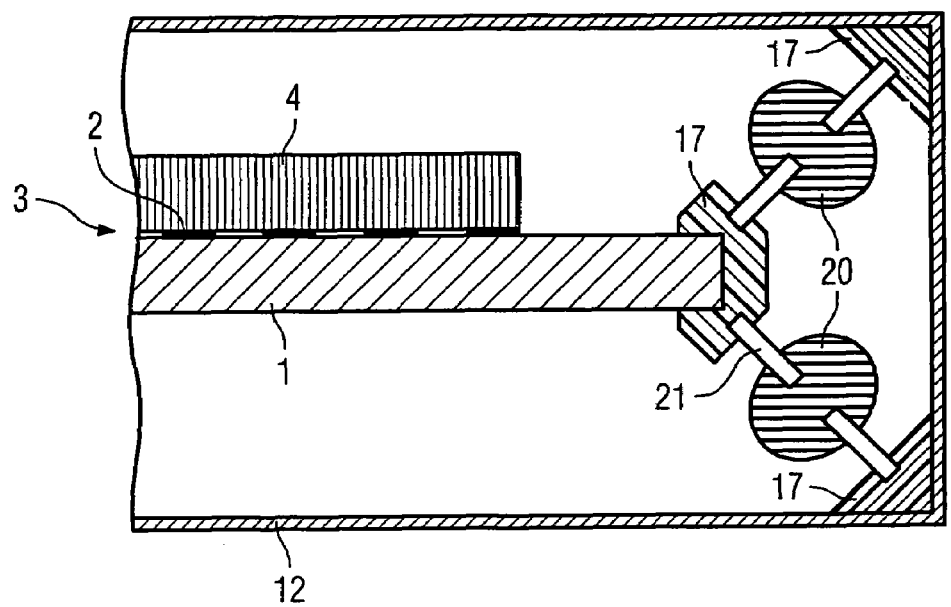
FIG. 8 shows a schematic partial sectional view of a fifth x-ray detector.

As can be seen from FIGS. 7 and 8, instead of the spring elements 18, rubber elements 20 may also be used. As shown in FIG. 8—these may be connected to the receiving elements 17 by means of plug-in elements 21.

Figure 9:
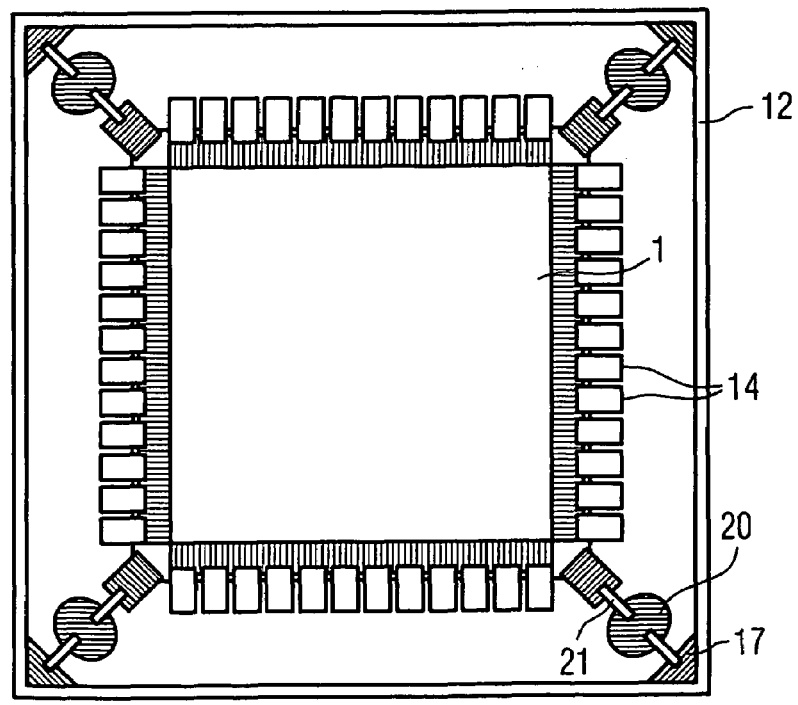
FIG. 9 shows a plan view of the x-ray detector according to FIG. 8.

FIG. 9 shows a plan view of the fifth x-ray detector. It can be seen from this that the detector plate 3 in particular is also mounted in a damped manner in the X/Y plane, shown here by way of the rubber elements 20. In the case of the exemplary embodiments shown in FIGS. 4 to 7, it is of course possible in the same way for the damping elements shown there, that is to say the spring elements 18 and the rubber elements 20, to be attached in the X/Y plane, in order to ensure completely damped mounting in the housing 12.

Figure 10:
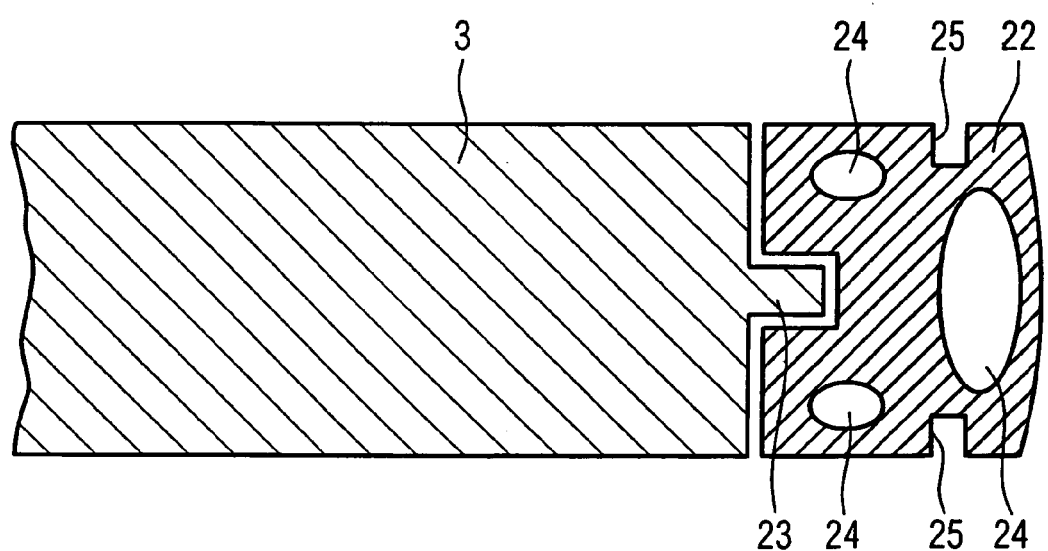
FIG. 10 shows a schematic partial sectional view of a sixth x-ray detector and FIG. 11 shows a schematic partial sectional view of a seventh x-ray detector.

FIG. 10 shows a schematic partial sectional view of a sixth x-ray detector. The detector plate 3 represented is surrounded by a peripheral absorption element 22 made of rubber. For anchorage in the absorption element 22, the detector plate 3 has lugs 23. For improved damping of vibrations or impact, the absorption element 22 has hollow chambers 24, which are filled with air. For anchorage in a housing 12 (not shown here), the absorption element 22 has clearances 25. Anchorage elements provided on the housing 12 may engage with an exact fit into the clearances 25.

Figure 11:
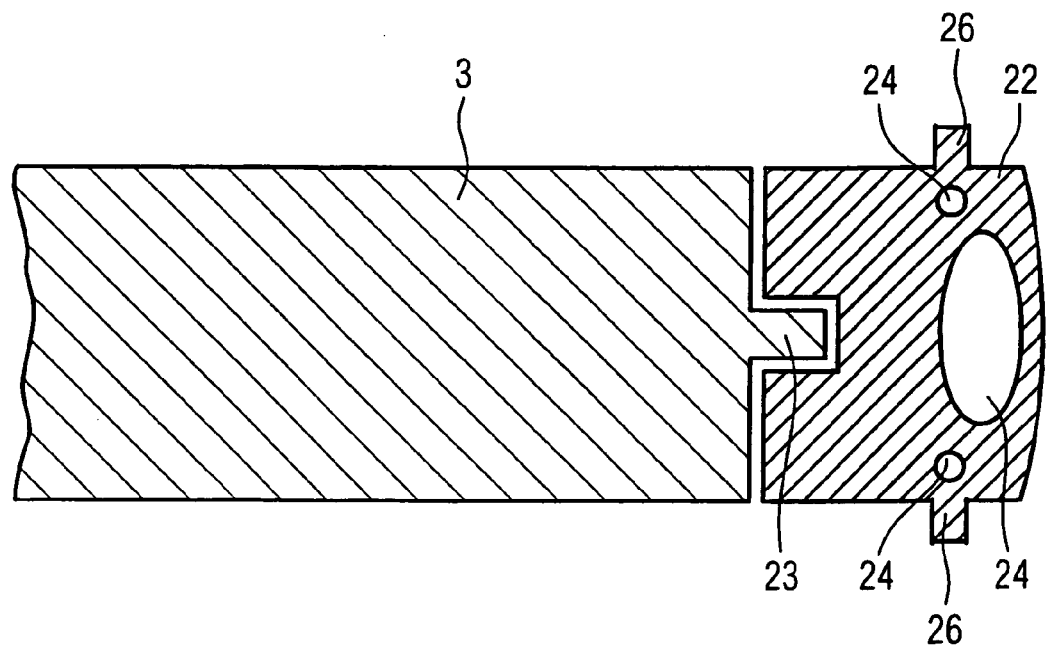

FIG. 11 shows a schematic partial view of a seventh x-ray detector, which differs from the sixth x-ray detector represented in FIG. 10 in that, instead of the clearances 25, the absorption element 22 has further lugs 26. For anchorage in a housing 12 (not shown here), the lugs 26 can engage with an exact fit into clearances of anchorage elements of the housing 12.

It is of course also possible to accommodate the detector plate 3, if appropriate together with the further substrate 13, in the housing 12 in a floating manner by using other damping elements. For example, it is conceivable to mount the detector plate 3 and/or the further substrate 13 in the housing 12 in a floating manner by using layers of foam. Such a floating mounting can be realized in a particularly simple and low-cost manner.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray detector, comprising:
   a detector plate, including a multiplicity of detector elements arranged in the X direction and the Y direction, accommodated in a cassette in a floating manner using at least one damping element that is produced from a material adapted to absorb impact energy by deforming;
   wherein an edge of the detector plate is peripherally surrounded by the damping element; and
   wherein the material includes at least one hollow chamber filled with air.

2. The x-ray detector as claimed in claim 1, wherein the detector plate includes a substrate.

3. The x-ray detector as claimed in claim 2, wherein detector elements produced from amorphous silicon are applied to the substrate.

4. The x-ray detector as claimed in claim 1, wherein electronics connected downstream of the detector elements are accommodated in the housing.

5. The x-ray detector as claimed in claim 4, wherein the detector plate includes a substrate and wherein the electronics are accommodated on a further substrate.

6. The x-ray detector as claimed in claim 5, wherein the further substrate is attached to the detector plate.

7. The x-ray detector as claimed in claim 5, wherein the further substrate is attached to the housing.

8. The x-ray detector as claimed in claim 5, wherein the detector plate is attached by use of the at least one damping element to at least one of an inside wall of the housing and to the further substrate.

9. The x-ray detector as claimed in claim 1, wherein the detector plate includes a substrate produced from glass.

10. The x-ray detector as claimed in claim 1, wherein the detector plate is attached by use of the damping element to at least one of an inside wall of the housing and to a substrate.

11. The x-ray detector as claimed in claim 1, wherein the at least one damping element is produced from a flexible material, adapted to absorb impact energy by deforming.

12. The x-ray detector as claimed in claim 1, wherein the at least one the damping element includes a plurality of damping elements.

* * * * *